(12) United States Patent
Hermetter et al.

(10) Patent No.: US 7,906,674 B2
(45) Date of Patent: Mar. 15, 2011

(54) OXIDIZED PHOSPHOLIPIDS

(76) Inventors: Albin Hermetter, Graz (AT); Michael Trenker, Salzburg (AT)

(*) Notice: Subject to any disclaimer, the term of this patent is extended or adjusted under 35 U.S.C. 154(b) by 169 days.

(21) Appl. No.: 11/996,969

(22) PCT Filed: Jul. 26, 2006

(86) PCT No.: PCT/AT2006/000317
§ 371 (c)(1),
(2), (4) Date: Feb. 28, 2008

(87) PCT Pub. No.: WO2007/012100
PCT Pub. Date: Feb. 1, 2007

(65) Prior Publication Data
US 2009/0130648 A1  May 21, 2009

(30) Foreign Application Priority Data

Jul. 27, 2005 (AT) ............................. A 1260/2005
Nov. 8, 2005 (AT) ............................. A 1826/2005

(51) Int. Cl.
*C07F 9/02* (2006.01)
(52) U.S. Cl. ............. 558/172; 548/405; 548/413; 435/4
(58) Field of Classification Search .................. 548/405, 548/413; 435/4; 558/172
See application file for complete search history.

(56) References Cited

U.S. PATENT DOCUMENTS 4,668,623 A * 5/1987 Kinnunen et al. .............. 435/19

FOREIGN PATENT DOCUMENTS

| EP | 1 318 154 | 6/2003 |
|---|---|---|
| JP | 2002-223794 | 8/2002 |
| WO | 00/32808 | 6/2000 |
| WO | 01/75170 | 10/2001 |

OTHER PUBLICATIONS www.abcam.com/technical., 2010.*
Puliikunnil et al.,2004, CAS: 141:363846.*
Kofune et al., 2000, CAS: 133:355202.*
Trenker, M. et al., "Fluorescence Microscopy Reveals Rapid Import of Oxidized Phospholipids into Vascular Smooth Muscle Cells," Joint Annual Meeting 2003: OGBM, ÖGGGT, ÖGBT, ANGT, Graz, Austria, Sep. 21, 2003, 4P-0973.
Kofune H et al: "Molecular recognition of vesicles containing pyrene compounds using fluorescence spectroscopy," Polymer Preprints, vol. 41, No. 2, Aug. 2000, pp. 1701-1702, XPOO1248221.
Kilpatrick P K et al: "Selective precipitation of antibody with ligand-modified phospholipids: Effect of lipid chain length," Biotechnology Progress, vol. 13, No. 4, Jul. 1997, pp. 446-452, XP002408845.
Kinsky S C et al: "Circumvention of the methotrexate transport system by methotrexate-phosphatidylethanolamine derivatives: Effect of fatty acid chain length," Biochimica et Biophysica ACTA, vol. 921, No. 1, 1987, pp. 96-103, XP002408846.
Vaz W L et al: "Translational diffusion of lipids in liquid crystalline phase phosphatidylcholine multibilayers. A comparison of experiment with theory." Biochemistry, vol. 24, No. 3, Jan. 29, 1985, pp. 781-786, XP002408847.
Vaz W L C et al: "Experimental evidence against the applicability of the Saffman-Delbrück model to the translational diffusion of lipids in phosphatidylcholine bilayer membranes," FEBS Letters, vol. 152, No. 2, Feb. 1983, pp. 287-290, XP009075372.

* cited by examiner

*Primary Examiner* — Rei-tsang Shiao
(74) *Attorney, Agent, or Firm* — Bradley Arant Boult Cummings, LLP

(57) ABSTRACT

The invention relates to oxidized phospholipids having one of the general formulas (I) or (II) wherein A=O, C, NH, or S; B=O, C, NH, or S; and $R_2$ is selected from the group consisting of —CO—$(CH_2)_n$—$CH_3$; —CO—$(CH_2)_n$—CHO; and —CO—$(CH_2)_n$—COOH, with n=3-7, with the proviso that in general formula (I), $R_1$ is selected from the group consisting of —$CH_2$—$(CH_2)_n$—X; and —CO—$(CH_2)_n$—X with n=5-11, wherein X is a fluorophore; and in general formula (II), $R_1$ is selected from the group consisting of —CH=CH—$(CH_2)_n$—$CH_3$ with n=9-15; —$(CH_2)_n$—$CH_3$ with n=11-17; and —CO—$(CH_2)_n$—$CH_3$ with n=10—16; and $R_3$ is selected from the group consisting of —CO—$(CH_2)_n$—X; and —$SO_2$—$(CH_2)_n$—X, with n=0-5, wherein X is a fluorophore.

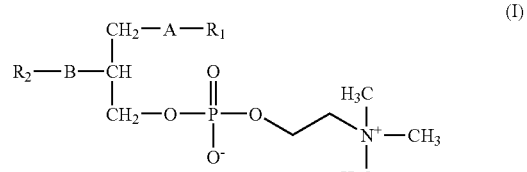

(I)

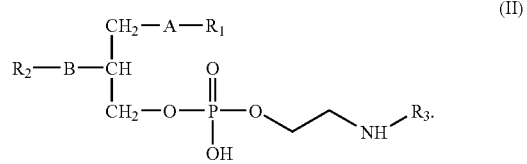

(II)

13 Claims, 5 Drawing Sheets

A

OXIDIZED PHOSPHOLIPIDS

BACKGROUND

Oxidative modification of LDL is considered an important pathogenetic factor in atherosclerosis. Studies from several laboratories have revealed that the biological effects triggered by mmLDL can largely be attributed to phospholipid oxidation products (Leitinger, N. et al. (1999) *PNAS* 96, 12010-12015; Watson, A. D. et al. (1995) *J. Clin. Invest.* 95, 774-782; Leitinger, N. et al. (1997) *Adv. Exp. Med. Biol.* 433, 379-382; Loidl, A. et al. (2003) *J. Biol. Chem.* 278, 32921-32928). Their increased levels in atherosclerotic plaques (Watson, A. D. et al. (1997) *J. Biol. Chem.* 272, 13597-13607; Itabe, H. et al. (1994) *J. Biol. Chem.* 269, 15274-15279) and the elevated antibody titers against oxidized phospholipids in humans and mice with lesions (Horkko, S. et al. (1999) *J. Clin. Invest.* 103, 117-128; Palinski, W. et al. (1995) *Arterioscler. Thromb. Vasc. Biol.* 15, 1569-1576; Palinski, W. et al. (1996) *J. Clin. Invest.* 98, 800-814) attract attention to the pathological relevance of these molecules.

A rapidly growing interest has been focused on two major representatives in the series of homologous oxidized phospholipids, namely 1-palmitoyl-2-glutaroyl-sn-glycero-3-phosphocholine (PGPC) and 1-palmitoyl-2-(5-oxovaleroyl)-sn-glycero-3-phosphocholine (POVPC). Their importance is stressed by the finding that they selectively activate processes in vascular wall cells that may contribute to the pathogenesis of atherosclerosis as well as other chronic inflammatory diseases. Both lipids were demonstrated to be 3- to 6-fold enriched in rabbit atherosclerotic lesions corresponding to approximately 62 and 116 ng/mg of aorta wet weight PGPC and POVPC, respectively (Subbanagounder, G. et al. (2000) *Arterioscler. Thromb. Vasc. Biol.* 20, 2248-2254).

In WO 01/75170 A a method of evaluating the risk for atherosclerosis is described, in which a biological sample comprising HDL is contacted with an oxidized phospholipid and the change in the amount of oxidized or non-oxidized phospholipid is measured, wherein the absence of change in the amount of oxidized phospholipid indicates a risk for atherosclerosis.

As mentioned above, oxidized phospholipids are involved in the pathogenesis of atherosclerosis. Oxidized phospholipids are further known to be hydrolytically cleaved by enzymes which are associated with lipoproteins and have antiatherogenetic activity, for example phospholipases or PAF acetylhydrolases.

SUMMARY

It is the object of the present invention to provide compounds which can be used to gather information about the activity of antiatherogenetic enzymes in a sample. In particular, their interaction with the enzymes should result in detectable products which allow to draw conclusions about the enzyme activity of the sample.

This object is achieved by an oxidized phospholipid having one of the general formulas I or II

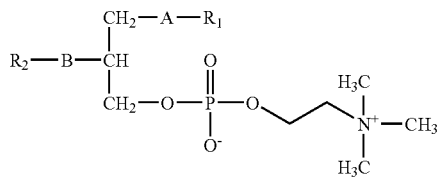

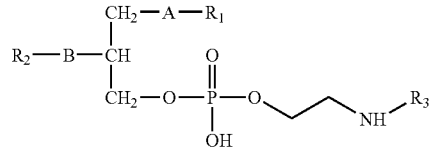

wherein
A=O, C, NH, or S;
B=O, C, NH, or S; and
$R_2$ is selected from the group consisting of —CO—$(CH_2)_n$—$CH_3$;
 —CO—$(CH_2)_n$—CHO; and
 —CO—$(CH_2)_n$—COOH, with n 3-7,
with the proviso that
in general formula I, $R_1$ is selected from the group consisting of
 —$CH_2$—$(CH_2)_n$—X; and
 —CO—$(CH_2)_n$—X with n=5-11, wherein X is a fluorophore; and
in general formula II, $R_1$ is selected from the group consisting of
 —CH=CH—$(CH_2)_n$—$CH_3$ with n=9-15;
 —$(CH_2)_n$—$CH_3$ with n=11-17; and
 —CO—$(CH_2)_n$—$CH_3$ with n=10-16;
and $R_3$ is selected from the group consisting of
 —CO—$(CH_2)_n$—X; and
 —$SO_2$—$(CH_2)_n$—X, with n=0-5, wherein X is a fluorophore.

DETAILED DESCRIPTION

Figure 1:
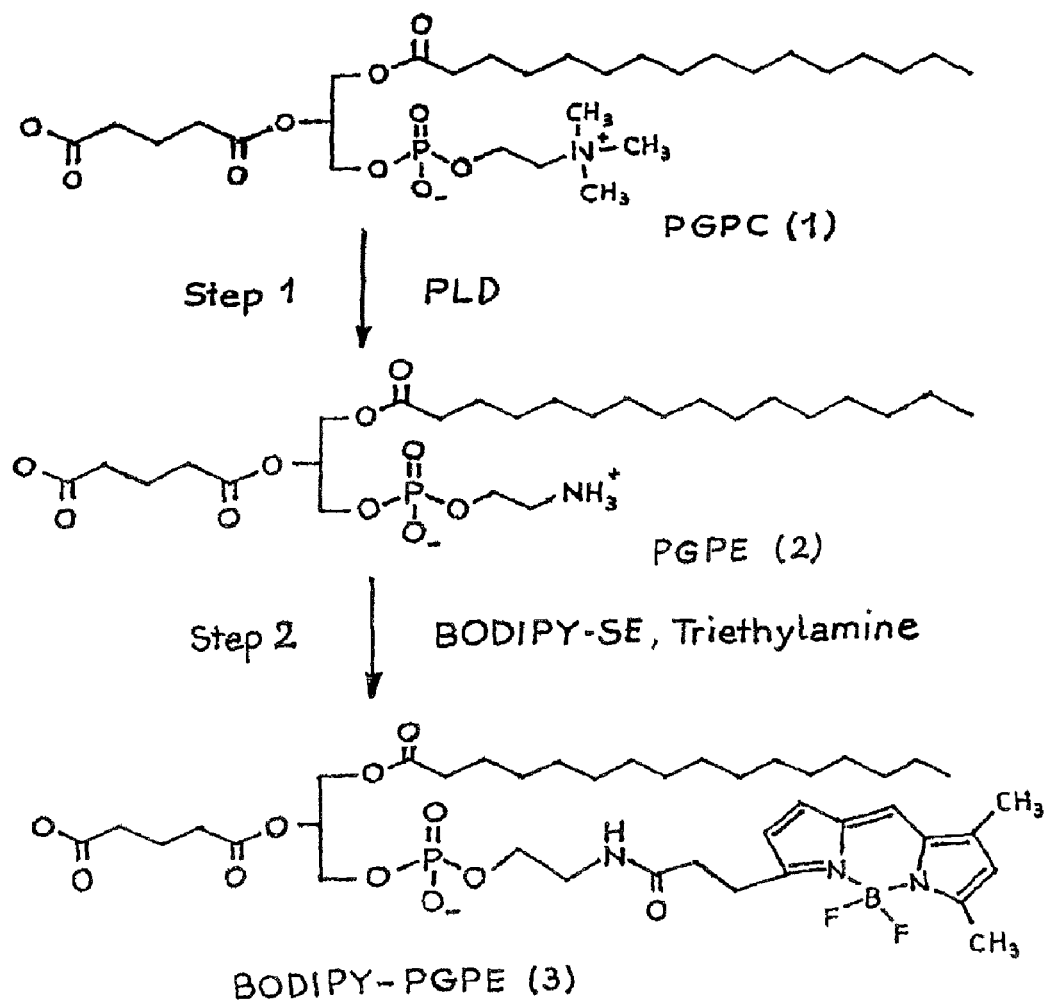
FIG. 1: Exemplary syntheses of BODIPY-PGPE and BODIPY-POVPE.

According to a preferred embodiment, A and/or B is oxygen.

According to another preferred embodiment, in general formula I, X is a fluorophore selected from the group consisting of pyrene, perylene and nitrobenzaxadiazole, and preferably is pyrene.

According to another preferred embodiment, in general formula II, X is a fluorophore selected from the group consisting of pyrene, perylene, borodiazaindacene (BODIPY™), cyanine dye 2, cyanine dye 3, cyanine dye 5 and Alexa dyes.

Preferred embodiments of oxidized phospholipids according to general formula I are the following compounds:
 1-(10-pyrenedecanoyl)-2-glutaroyl-sn-glycero-3-phosphocholine (PyrGPC)
 1-(10-pyrenedecanoyl)-2-(5-oxovaleroyl)-sn-glycero-3-phosphocholine (PyrOVPC)

Preferred embodiments of oxidized phospholipids according to general formula II are the following compounds:
- 1-palmitoyl-2-glutaroyl-sn-glycero-3-phospho-N-(3-[4,4-difluoro-4-bora-3a,4a-diaza-s-indacene]-propionyl)-ethanolamine (BODIPY-PGPE)
- 1-palmitoyl-2-glutaroyl-sn-glycero-3-phospho-N-(Alexa Fluor 647-carbonyl)-ethanolamine (Alexa647-PGPE)
- 1-palmitoyl-2-oleoyl-sn-glycero-3-phospho-N-(3-[4,4-difluoro-4-bora-3a,4a-diaza-s-indacene]-propionyl)-ethanolamine (BODIPY-POPE)
- 1-palmitoyl-2-(5-oxovaleroyl)-sn-glycero-3-phospho-N-(3-[4,4-difluoro-4-bora-3a,4a-diaza-s-indacene]-propionyl)-ethanolamine (BODIPY-POVPE)

It has been found that the fluorescently labeled oxidized phospholipids according to the invention can be used as substrates for enzymes having antiatherogenetic activity. The claimed compounds are particularly useful for the diagnostic determination of these enzymes in blood samples. The fluorescently labeled cleavage products resulting from interaction of the oxidized phospholipids with the enzymes in question can be easily and sensitively determined by chromatographic analysis such as HPLC and thereby provide information about the enzyme activities present in the sample.

Another aspect of the invention thus refers to the use of the oxidized phospholipid according to the invention for determining the presence of enzymes having antiatherogenetic activity, preferably phospholipases or PAP-acetylhydrolases, in a sample.

A further aspect of the invention refers to a method for determining the presence of enzymes having antiatherogenetic activity in a sample comprising adding oxidized phospholipid according to the invention to the sample and subjecting the sample to chromatographic analysis, preferably HPLC.

The present invention will be explained in more detail by way of the following examples and the attached drawings.

EXAMPLES

Synthesis of Fluorescent Oxidized Phospholihids

Preparation of 1-palmitoyl-2-glutaroyl-sn-glycero-3-phospho-N-(3-[4,4-difluoro-4-bora-3a,4a-diaza-s-indacene]-propionyl)-ethanolamine (BODIPY-PGPE)

1. Synthesis of 1-palmitoyl-2-glutaroyl-sn-glycero-3-phosphocholine (PGPC)

PGPC (FIG. 1A, 1) was synthesized according to a modified version of the procedure by Watson et al. (*J. Biol. Chem.* 272, 13597-13607, 1997) and Subbanagounder et al. (*Free Radic. Biol. Med.* 28, 1751-1761, 2000). A solution of dry 1-palmitoyl-sn-glycero-3-phosphocholine (62 mg, 125 µmol), dry glutaric anhydride (70 mg, 613 µmol, 5 eq) and DMAP (p-(N,N'-dimethylamino)pyridine, 75 mg, 614 µmol, 5 eq) in 6 ml of anhydrous dichloromethane was magnetically stirred over night at 35° C. The reaction was monitored by TLC with CHCl$_3$/MeOH/25% NH$_3$ (65:35:5, v/v/v) as a developing system, and quenched by addition of 3 ml of MeOH. The resulting mixture was washed once with 1.8 ml of MeOH/H$_2$O (1:1, v/v). After evaporation of the organic phase, excess DMAP was removed by trituration with 4 ml of diethylether. Removal of the supernatant afforded 32 mg of PGPC (42%, $R_f$=0.05).

2. Synthesis of 1-palmitoyl-2-glutaroyl-sn-glycero-3-phosphoethanolamine (PGPE)

PGPE (FIG. 1A, 2) was obtained by transphosphatidylation of PGPC (90 mg, 148 µmol) (FIG. 1A, 1) by PLD (phospholipase D, 29 units) in an emulsion of 1.4 ml of toluene and 4.3 ml of a 0.5 M sodium acetate buffer (pH 7.2) containing 0.5 M ethanolamine (FIG. 1A, step 1). The biphasic system was stirred at 35° C. over night. The reaction was monitored by TLC and quenched by addition of 4.3 ml of MeOH. The product was extracted with 43 ml of CHCl$_3$/MeOH (2:1, v/v). The organic phase was washed twice with 11 ml of MeOH/H$_2$O (1:1, v/v) to remove excess ethanolamine, evaporated and subjected to preparative TLC. The product was scraped off and eluted three times from the silica gel with CHCl$_3$/MeOH (1:4, v/v). Evaporation of the combined extracts yielded the desired product (30.3 mg, 36%, $R_f$=0.30).

3. Synthesis of 1-palmitoyl-2-glutaroyl-sn-glycero-3-phospho-N-(3-[4,4-difluoro-4-bora-3a,4a-diaza-s-indacene]-propionyl)-ethanolamine (BODIPY-PGPE)

Figure 2:
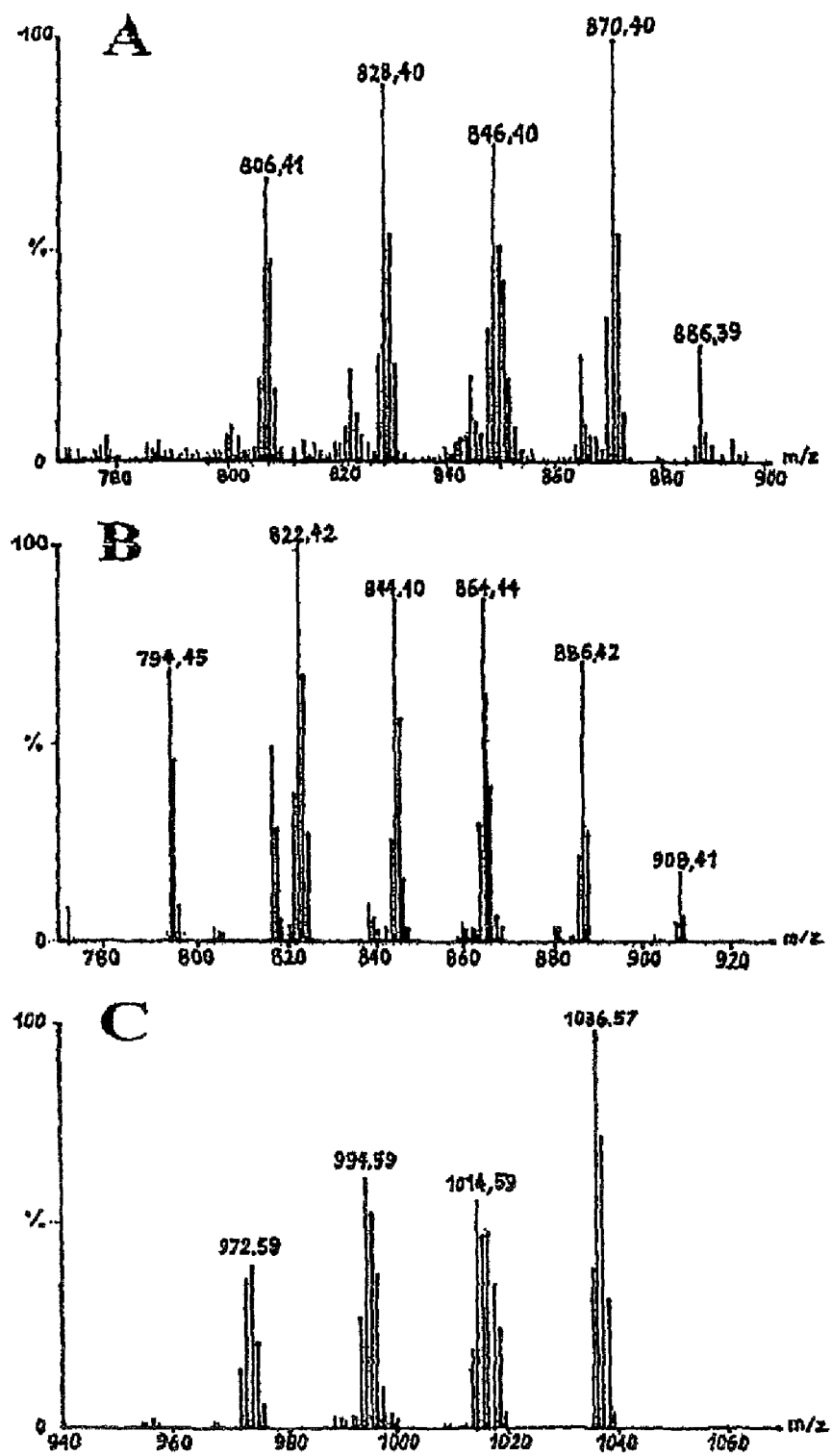
FIG. 2: Mass spectra of BODIPY-POVPE, BODIPY-PGPE and BODIPY-POPE.
Figure 3:
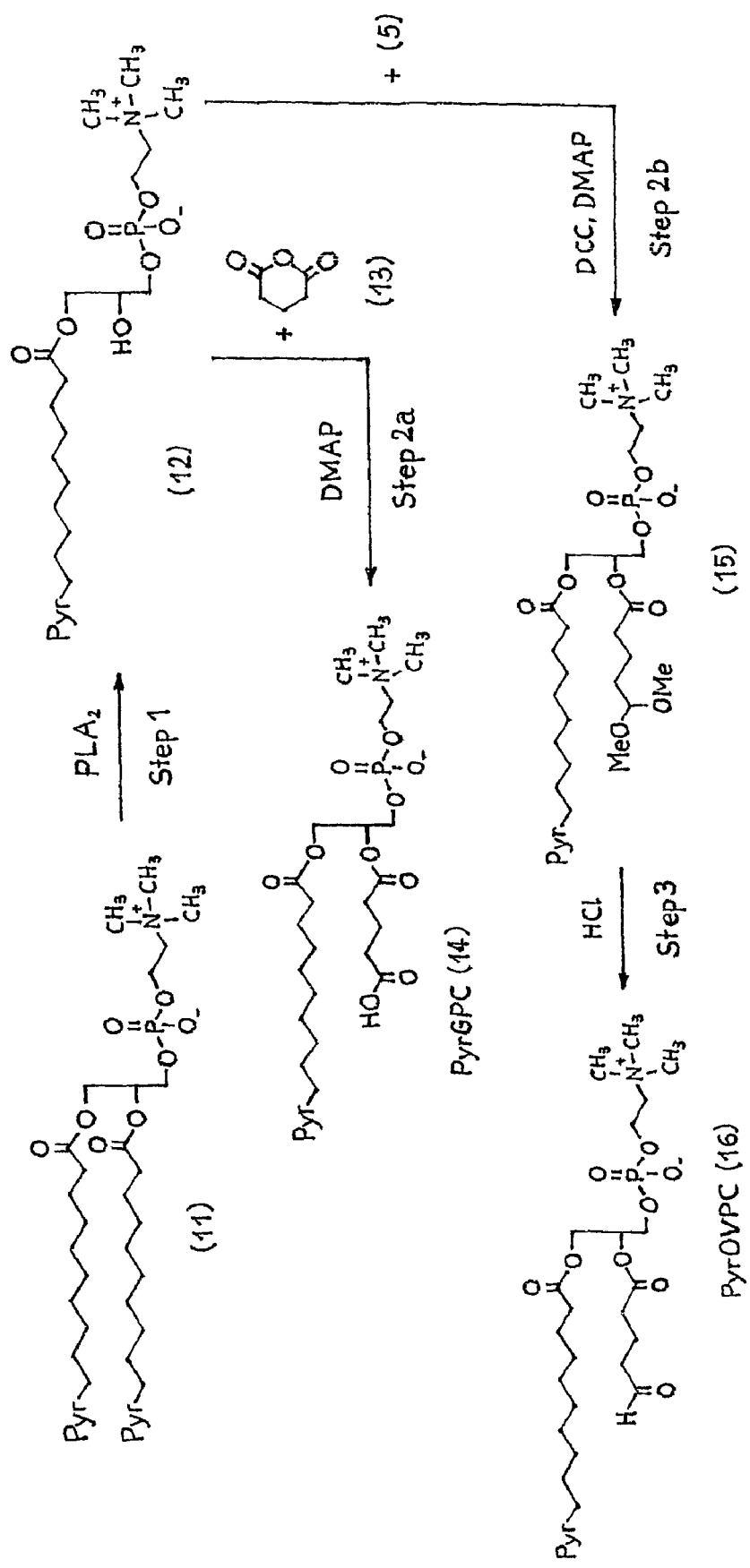
FIG. 3: Exemplary synthesis of PyrOVPC.

To a magnetically stirred solution of BODIPY-SE (4,4-difluoro-5,7-dimethyl-4-bora-3a,4a-diaza-s-indacene-propionic acid succinimidyl ester, 0.96 mg, 2.5 µmol) in 1 ml of CHCl$_3$/MeOH (2:1, v/v) were added PGPE (4.4 mg, 7.8 µmol, 3 eq) (FIG. 1A, 2) and triethylamine p.a. (10 µl, 72 µmol, 30 eq) (FIG. 1A, step 2). Then the flask was flushed with nitrogen, protected from light, and the resulting solution was stirred at room temperature for 1 h. The progress of the reaction was monitored by TLC. The solvent was removed under a nitrogen stream until a volume of 400 µl was reached, from which the lipid was purified by preparative TLC. The desired compound was visualized under UV light, scraped off the TLC plate and eluted three times from the silica gel with CHCl$_3$/MeOH (1:4, v/v). The solvent was removed from the combined extracts by rotary evaporation to afford BODIPY-PGPE (1.77 mg, 85%, $R_f$=0.28) (FIG. 1A, 3).

Preparation of 1-palmitoyl-2-glutaroyl-sn-glycero-3-phospho-N-(Alexa647-carbonyl)-ethanolamine (Alexa647-PGPE)

Alexa647-PGPE corresponds to BODIPY-PGPE (FIG. 1A, 3) but contains Alexa647 instead of BODIPY at its head group. It was obtained from Alexa647-SE (Alexa Fluor 647 carboxylic acid succinimidyl ester, 0.5 mg, 0.4 µmol) and PGPE (0.68 mg, 1.2 µmol, 3 eq) (FIG. 1A, 2) in 0.5 ml of CHCl$_3$/MeOH (2:1, v/v) after addition of triethylamine p.a. (5 µl, 36 µmol, 90 eq) followed by stirring at room temperature for 90 min. The reaction mixture was strictly protected from light. The progress of the reaction was monitored by TLC (RP-18 F$_{254s}$; Merck, Darmstadt, Germany). The product was purified by preparative TLC with H$_2$O/EtOH/n-propanol (20:57:23, v/v/v) as a developing system, scraped off and eluted twice with CHCl$_3$/MeOH (1:1, v/v) and once with MeOH. Removal of the solvent under a stream of nitrogen provided Alexa647-PGPE (0.26 µmol, 65%, $R_f$=0.80).

Preparation of 1-palmitoyl-2-(5-oxovaleroyl)-sn-glycero-3-phospho-N-(3-[4,4-difluoro-4-bora-3a,4a-diaza-s-indacene]-propionyl)-ethanolamine (BODIPY-POVPE)

Figure 1B:
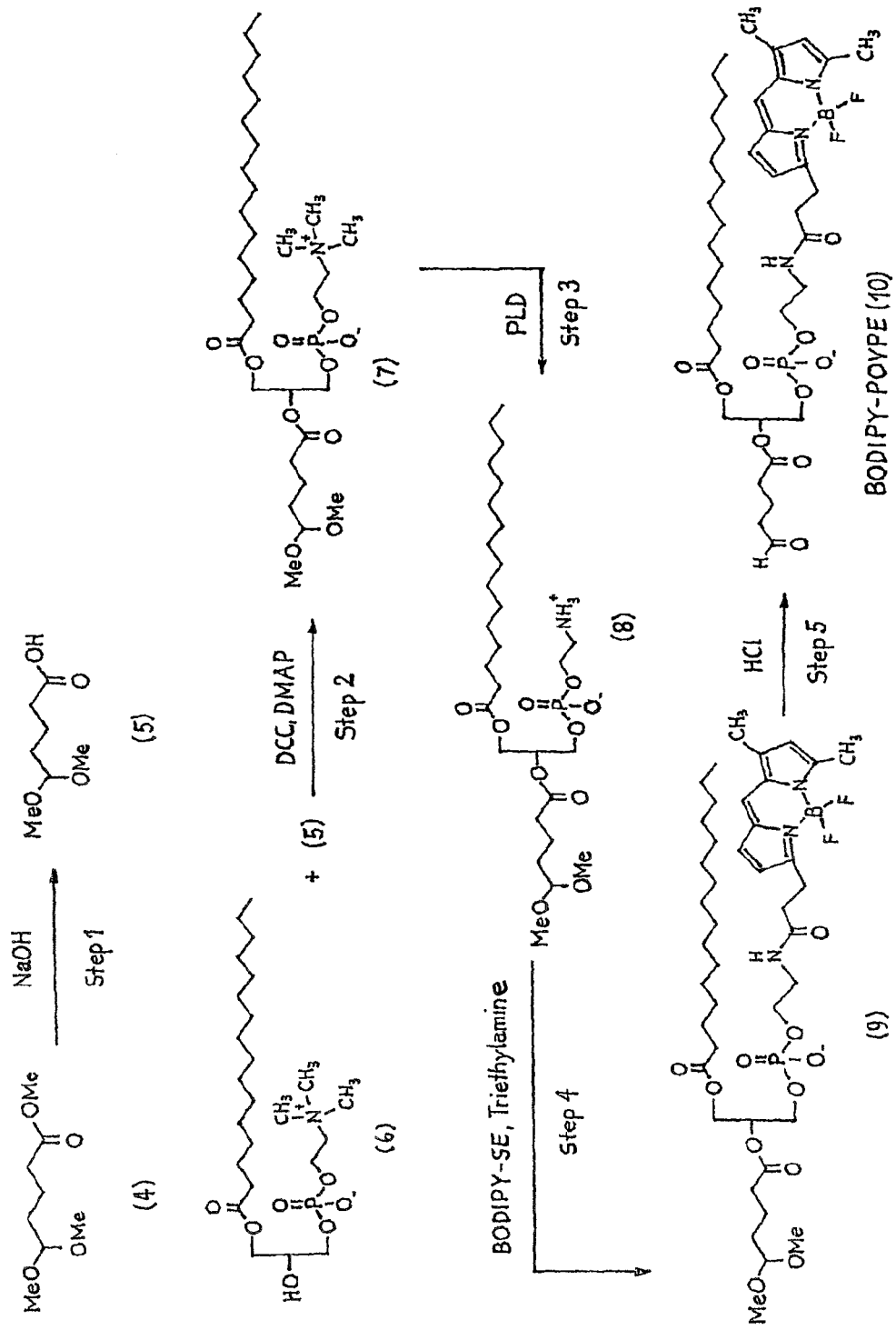

1. Synthesis of 1-palmitoyl-2-(5-dimethoxypentanoyl)-sn-glycero-3-phosphoethanolamine A solution of 5,5-dimethoxypentanoic acid methyl ester (220 mg, 1.25 mmol) (FIG. 1B, 4) and sodium hydroxide (250 mg, 6.25 mmol, 5 eq) in 5 ml of H$_2$O/MeOH/THF (2:5:3, v/v/v) was stirred at room temperature for 90 min (FIG. 1B, step 1). After cooling down to 0° C., the reaction mixture was acidified to pH 2.1 by subsequent addition of 6 ml of 1 N and appropriate amounts of 0.1 N HCl and then extracted with dichloromethane (3×15 ml). The combined organic extracts were washed with water (2×10 ml) and dried over Na$_2$SO$_4$. The solvent was removed under reduced pressure except for 10-15 ml containing the desired product ($R_f$=0.35) (FIG. 1B, 5), which was immediately used for the acylation reaction without further purification. 1-Palmitoyl-sn-glycero-3-phosphocholine (209 mg, 0.42 mmol) (FIG. 1B, 6), DCC (N,N'-dicyclohexylcarbodiimide, 270 mg, 1.3 mmol, 3 eq) and DMAP (160 mg, 1.3 mmol, 3 eq) were added to this solution of 5,5-dimethoxypentanoic acid (FIG. 1B, step 2). The mixture was stirred under nitrogen at room temperature over night. The reaction was monitored by TLC. After addition of 6 ml of MeOH, the organic solution was washed twice with MeOH/$H_2O$ (1:1, v/v). The solvent was removed under vacuum, and traces of water were evaporated after addition of benzene/EtOH (3:2, v/v). The oily residue was flash chromatographed on 12 g silica gel with $CHCl_3$/MeOH/25% $NH_3$ (65:35:5, v/v/v) as a solvent to give 1-palmitoyl-2-(5-dimethoxypentanoyl)-sn-glycero-3-phosphocholine (245 mg, 91%, $R_f$=0.14) (FIG. 1B, 7). The ethanolamine analog (FIG. 1B, 8) was obtained by transphosphatidylation of the choline lipid as described previously for the conversion of PGPC to PGPE (compare FIG. 1A, step 1) (yield: 6.2 mg, 66%, $R_f$=0.24 using $CHCl_3$/MeOH/25% $NH_3$, 65:35:5, v/v/v as a developing solvent) (FIG. 1B, step 3).

2. Synthesis of 1-palmitoyl-2-(5-oxovaleroyl)-sn-glycero-3-phospho-N-(3-[4,4-difluoro-4-bora-3a,4a-diaza-s-indacene]-propionyl)-ethanolamine (BODIPY-POVPE)

Triethylamine p.a. (10 µl, 72 µmol, 14 eq) was added to a solution of 1-palmitoyl-2-(5-dimethoxypentanoyl)-sn-glycero-3-phosphoethanolamine (3.0 mg, 5.0 µmol) (FIG. 1B, 8) and BODIPY-SE (1.95 mg, 5.0 µmol, 1 eq) in 1 ml of $CHCl_3$/MeOH (2:1, v/v) (FIG. 1B, step 4). The reaction mixture was stirred at room temperature for 80 min. The solvent was removed under vacuum yielding 1-palmitoyl-2-dimethoxypentanoyl-sn-glycero-3-phospho-N-(3-BODIPY-propionyl)-ethanolamine (FIG. 1B, 9) that was suitable for the next reaction without further purification. Release of the desired product was accomplished by acetal cleavage of this stable precursor (2.0 mg, 2.3 µmol) with 400 µl of THF/HCl (1 N) (FIG. 1B, step 5). After only 2 min, the reaction mixture was neutralized with $NaHCO_3$ followed by extraction of the product with 1.2 ml of $CHCl_3$/MeOH (2:1, v/v). The organic phase was washed twice with 300 µl of water, dried over $Na_2SO_4$ and evaporated under reduced pressure leading to 1.65 mg of BODIPY-POVPE (87%, $R_f$=0.22 using $CHCl_3$/MeOH/$H_2O$, 15:5:0.1, v/v/v as a developing system) (FIG. 1B, 10).

Preparation of 1-palmitoyl-2-oleoyl-sn-glycero-3-phospho-N-(3-[4,4-difluoro-4-bora-3a,4a-diaza-s-indacene]-propionyl)-ethanolamine (BODIPY-POPE)

BODIPY-SE (1.00 mg, 2.57 µmol), triethylamine p.a. (10 µl, 72 µmol, 28 eq) and POPE (1-palmitoyl-2-oleoyl-sn-glycero-3-phosphoethanolamine, 5.53 mg, 7.70 µmol, 3 eq) were dissolved in 1 ml of $CHCl_3$/MeOH (2:1, v/v). The mixture was stirred at room temperature for 60 min, then the solvent was removed under a stream of nitrogen. The white oily residue was dissolved in 500 µl of $CHCl_3$/MeOH (2:1, v/v). The product was purified by preparative TLC. The fluorescent band containing the product was scraped off the plate and eluted three times with $CHCl_3$/MeOH (1:4, v/v). The combined extracts were evaporated to deliver the desired product (1.31 mg, 51%, $R_f$=0.59).

Synthesis of 1-(10-pyrenedecanoyl)-2-glutaroyl-sn-glycero-3-phosphocholine (PyrGPC)

To a magnetically stirred emulsion of 1,2-bis(10-pyrenedecanoyl)-sn-glycero-3-phosphocholine (45 mg, 47 µmol) (FIG. 3, 11) in a mixture of 3 ml of 0.1 M Tris-HCl buffer (pH 8) containing 0.1 M $CaCl_2$ and 3 ml of diethylether (peroxide-free) were added 50 units of $PLA_2$ (Naja naja venom) (FIG. 3, step 1). The reaction mixture was stirred overnight at 35-40° C. After removing the diethylether, the product was extracted from the aqueous solution with $CHCl_3$/MeOH (2:1, v/v) (3×5 ml). The combined organic fractions were evaporated and the residual water was removed under high vacuum leading to 50 mg of a mixture of 1-(10-pyrenedecanoyl)-sn-glycero-3-phosphocholine (FIG. 3, 12) and free pyrenedecanoic acid. The latter one was removed by trituration with diethylether. After removal of the solvent under vacuum, 25 mg of the pure lysophospholipid were obtained (88%, $R_f$=0.12 in $CHCl_3$/MeOH/AcOH/$H_2O$, 50:30:10:5, v/v/v/v as a developing system). Glutaric anhydride (12 mg, 105 µmol, 11 eq) and anhydrous DMAP (4 mg, 33 µmol, 3 eq) were added to a solution of the lysophospholipid (6.0 mg, 9.8 µmol) in 3 ml of anhydrous dichloromethane (FIG. 3, step 2a). The reaction was stirred over night at 35-40° C. Flash chromatography of the crude product on 10 g of silica gel with $CHCl_3$/MeOH/$H_2O$ (65:25:4, v/v/v) led to PyrGPC (2.2 mg, 31%, $R_f$=0.18 in $CHCl_3$/MeOH/AcOH/$H_2O$, 50:30:10:5, v/v/v/v as a developing system) (FIG. 3, 14).

Synthesis of 1-(10-pyrenedecanoyl)-2-(5-oxovaleroyl)-sn-glycero-3-phosphocholine (PyrOVPC)

1-(10-Pyrenedecanoyl)-sn-glycero-3-phosphocholine (10 mg, 16 µmol) (FIG. 3, 12) was acylated with 5,5-dimethoxypentanoic acid (acid "5") in 10 ml of dichloromethane containing DCC (200 mg, 1.0 mmol, 59 eq) and DMAP (200 mg, 1.6 mmol, 100 eq). The reaction mixture was stirred at room temperature over night (FIG. 3, step 2b). The progress of the reaction was monitored by TLC until the reaction was stopped by addition of 6 ml of MeOH. The resultant solution was washed twice with MeOH/$H_2O$ (1:1, v/v), and the solvent was removed under reduced pressure. The crude product was purified by preparative TLC, scraped off and eluted five times with 4 ml of $CHCl_3$/MeOH (1:4, v/v). Residual silica gel was removed by washing the combined organic fractions (concentrated to a volume of 5 ml) with 1 ml of MeOH/$H_2O$ (1:1, v/v). Evaporation of the solvent yielded 6 mg of 1-(10-pyrenedecanoyl)-2-(5-dimethoxypentanoyl)-sn-glycero-3-phosphocholine (49%, $R_f$=0.17) (FIG. 3, 15). Deprotection of intermediate 15 (5.6 mg, 7.4 µmol) was accomplished by acetal cleavage with THF/HCl (1 N), followed by neutralization with $NaHCO_3$ and extraction of the product with $CHCl_3$/MeOH (2:1, v/v). The organic phase was washed twice, dried over $Na_2SO_4$ and evaporated under reduced pressure leading to 1.1 mg of PyrOVPC (21%, $R_f$=0.05) (FIG. 3, step 3).

Mass Spectrometry

Figure 4:
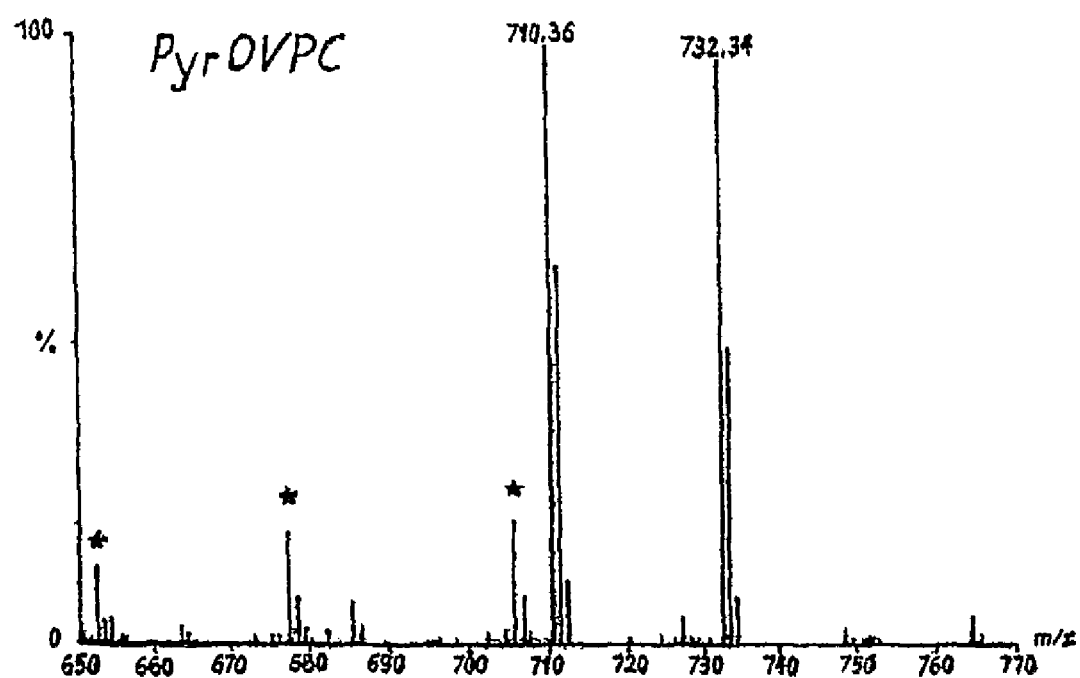
FIG. 4: Mass spectra of PyrGPC and PyrOVPC.
Figure 4:
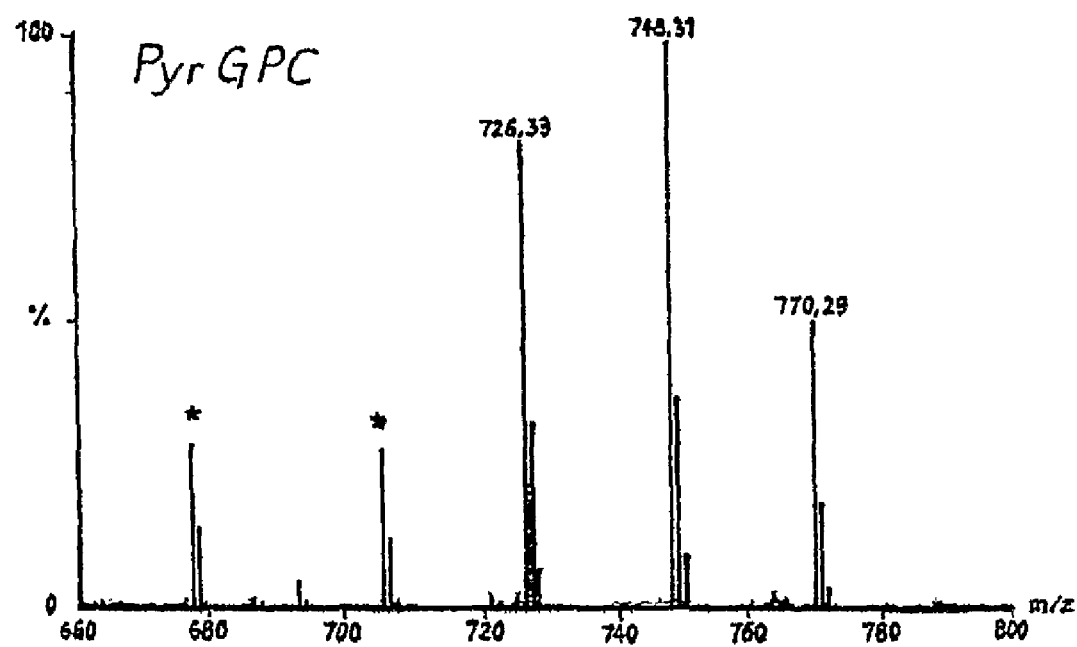

Matrix assisted laser desorption/ionisation time-of-flight (MALDI-TOF) mass spectra were performed on a Micromass TofSpec2E equipped with a nitrogen laser ($\lambda$=337 nm, operated at 5 Hz) and a time-lag focusing unit. Ions were generated by irradiation just above the threshold laser power. The spectra were recorded in the reflectron mode with an acceleration voltage of 20 kV and externally calibrated with a suitable mixture of poly(ethylene glycol)s (PEG). Samples were typically prepared by mixing solutions of the matrix (2,5-dihydroxybenzoic acid, c=10 mg/ml, $CH_3CN$/0.1% trifluoroacetic acid (TFA), 70:30, v/v), the analyte (c=0.01-1 mg/ml, $CHCl_3$/MeOH, 2:1, v/v) and NaTFA (c=1 mg/ml, $CH_3CN$/$H_2O$, 70:30, v/v) in a ratio of 10:1:0.5 (v/v/v). A 0.5 µl aliquot of the mixture was deposited on the sample plate (stainless steel) and allowed to dry under air. The spectra of 50-100 shots were averaged to improve the signal-to-noise ratio. All m/z values discussed in this work correspond to the most intense peak of any isotope distribution. The mass spectra of BODIPY-POVPE, BODIPY-PGPE and BODIPY-POPE are shown in FIG. 2. The mass spectra of PyrGPC and PyrOVPC are shown in FIG. 4.

The invention claimed is:

1. An oxidized phospholipid having one of the general formulas I or II

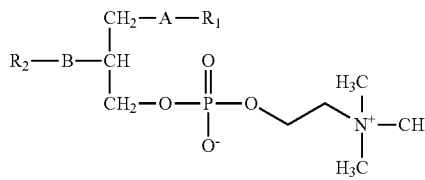

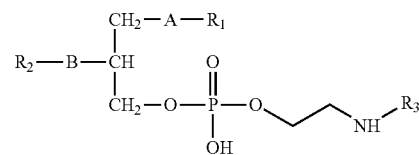

Wherein
A=O, C, NH, or S;
B=O, C, NH, or S; and
$R_2$ is selected from the group consisting of —CO—$(CH_2)_n$—$CH_3$;
—CO—$(CH_2)_n$—CHO; and
—CO—$(CH_2)_n$—COOH, with n=3-7,
with the proviso that
in general formula I, $R_1$ is selected from the group consisting of
—$CH_2$—$(CH_2)_n$—X; and
—CO—$(CH_2)_n$—X with n=5-11, wherein X is a fluorophore; and
in general formula II, $R_1$ is selected from the group consisting of
—CH=CH—$(CH_2)_n$—$CH_3$ with n=9-15;
—$(CH_2)_n$—$CH_3$ with n=11-17; and
—CO—$(CH_2)_n$—$CH_3$ with n=10-16;
and $R_3$ is selected from the group consisting of
—CO—$(CH_2)_n$—X; and
—$SO_2$—$(CH_2)_n$—X, with n=0-5, wherein X is a fluorophore.

2. The oxidized phospholipid of general formula I according to claim 1, wherein A and/or B is oxygen.

3. The oxidized phospholipid of general formula I according to claim 1, wherein X is a fluorophore selected from the group consisting of pyrene, perylene and nitrobenzaxadiazole, and preferably is pyrene.

4. The oxidized phospholipid of general formula I according to claim 1, characterized as 1-(10-pyrenedecanoyl)-2-glutaroyl-siz-glycero-3-phosphocholine (PyrGPC).

5. The oxidized phospholipid of general formula I according to claim 1, characterized as 1-(10-pyrenedecanoyl)-2-(5-oxovaleroyl)-sn-glycero-3-phosphocholine (PyrOVPC).

6. A method for determining the presence of enzymes having antiatherogenetic activity in a sample comprising adding oxidized phospholipid of general formula I according to claim 1 to the sample and subjecting the sample to chromatographic analysis, preferably HPLC.

7. The oxidized phospholipid of general formula II according to claim 1, wherein A and/or B is oxygen.

8. The oxidized phospholipid of general formula II according to claim 1, wherein X is a fluorophore selected from the group consisting of pyrene, perylene, borodiazaindacene (BODIPY™), cyanine dye 2, cyanine dye 3, cyanine dye 5 and Alexa dyes.

9. The oxidized phospholipid of general formula II according to claim 1, characterized as 1-palmitoyl-2-glutaroyl-sn-glycero-3-phospho-N-(3-[4,4-difluoro-4-bora-3a-,4a-diaza-s-indacene]-propionyl)-ethanolamine (BODIPY-PGPE).

10. The oxidized phospholipid of general formula II according to claim 1, characterized as 1-palmitoyl-2-glutaroyl-sn-glycero-3-phospho-N-(Alexa Fluor 647-carbonyl)-ethanolamine (Alexa 647-PGPE).

11. The oxidized phospholipid of general formula II according to claim 1, characterized as 1-palmitoyl-2-oleoyl-sn-glycero-3-phospho-N-(3-[4,4-difluoro-4-bora-3a,4a-diaza-s-indacene]-propionyl)-ethanolamine (BODIPY-POPE).

12. The oxidized phospholipid of general formula II according to claim 1, characterized as 1-palmitoyl-2-(5-oxovaleroyl)-sn-glycero-3-phospho-N-(3-[4,4-difluoro-4-bora-3 a,4a-diaza-s-indacene]-propionyl)-ethanolamine (BODIPY-POVPE).

13. A method for determining the presence of enzymes having antiatherogenetic activity in a sample comprising adding oxidized phospholipid of general formula II according to claim 1, to the sample and subjecting the sample to chromatographic analysis, preferably HPLC.

* * * * *